(12) United States Patent
Webb et al.

(10) Patent No.: US 7,521,198 B1
(45) Date of Patent: Apr. 21, 2009

(54) COMPOSITIONS AND METHODS FOR DETECTING AND TREATING ATHEROSCLEROSIS

(75) Inventors: Nancy R. Webb, Lexington, KY (US); Frederick C. DeBeer, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 296 days.

(21) Appl. No.: 10/445,320

(22) Filed: May 27, 2003

Related U.S. Application Data (60) Provisional application No. 60/382,563, filed on May 24, 2002.

(51) Int. Cl.
*G01N 33/573* (2006.01)

(52) U.S. Cl. .................. 435/7.24; 435/7.4; 435/960

(58) Field of Classification Search ................ 424/1.49, 424/9.34, 9.411; 435/7.24, 7.4, 960
See application file for complete search history.

(56) References Cited

U.S. PATENT DOCUMENTS 6,716,410 B1 * 4/2004 Witztum et al. ............ 424/1.49

2003/0100524 A1 * 5/2003 Bennett et al. ................ 514/44
2003/0152513 A1 * 8/2003 Blankenberg et al. ...... 424/1.49
2004/0120893 A1 * 6/2004 Witztum et al. ............ 424/1.49

OTHER PUBLICATIONS

K. Öörni et al., "Aggregation, fusion, and vesicle formation or modified low density lipoprotein particles: molecular mechanisms and effects on matrix interactions", Journal of Lipid Research, vol. 41, 2000, pp. 1703-1714.
D.A. Six et al., "The expanding superfamily of phospholipase $A_2$ enzymes: classification and characterization", Biochimica et Biophysica Acta, 1488, (2000), pp. 1-19.
M.A. Balboa et al., "Novel Group V Phospholipase $A_2$ Involved in Arachidonic Acid Mobilization in Murine $P388D_1$ Macrophages", The Journal of Biological Chemistry, vol. 271, No. 50, Issue of Dec. 13, 1996, pp. 32381-32384.
R.M. Kramer et al., "Structure and Properties of a Human Non-pancreatic Phospholipase $A_2$", The Journal of Biological Chemistry, vol. 264, No. 10, Issue of Apr. 5, 1989, pp. 5768-5775.
N.R. Webb et al., "Macorphage-Expressed Group IIA Secretory Phospholipase $A_2$ Increases Atherosclerotic Lesion Formation in LDL Receptor-Deficient Mice", Arterioscler Thromb Vasc Biol, pp. 263-288.

* cited by examiner

*Primary Examiner*—David A Saunders
(74) *Attorney, Agent, or Firm*—McDermott Will & Emery LLP (57) ABSTRACT

Methods for detecting atherosclerotic plaque and quantifying the amount of Group V $sPLA_2$ in plasma are disclosed. These methods can be used to assess the risk of cardiovascular pathology in a patient.

4 Claims, 8 Drawing Sheets

Fig. 1. Proposed model for the role of Group V sPLA$_2$ in promoting macrophage foam cell formation.

FIGURE 8 unmodified LDL mock-hydrolyzed LDL vortexed LDL

Group V sPLA$_2$-LDL

COMPOSITIONS AND METHODS FOR DETECTING AND TREATING ATHEROSCLEROSIS

This application claims the benefit of priority to Provisional Application 60/382,563, filed May 24, 2002, which is incorporated by reference in its entirety.

FIELD OF THE INVENTION

The invention relates to compositions and methods for the detection and treatment of atherosclerosis. In particular, the invention relates to compositions containing an inhibitor or antibody that binds specifically to Group V secretory phospholipase (sPLA2).

BACKGROUND OF THE INVENTION

A critical event in early atherogenesis is the retention of low density lipoprotein (LDL) particles in the subendothelium through their binding intimal proteoglycans. These retained lipoprotein particles are exposed to several modifying enzymes in the arterial wall, including lipases, oxidizing enzymes, and proteases. A multitude of biological responses to such modified LDL, including the recruitment and lipid loading of macrophages, leads to the initiation and progression of atherosclerosis. The extracellular matrix (ECM) appears to play an active role in this process by not only mediating the retention of LDL particles, but by also modulating the activity of various enzymes towards LDL. Thus, in regions where LDL is being accumulated, the co-localization of LDL, ECM and LDL modifying enzymes leads to a self-perpetuating cascade of events that culminates in atherosclerosis.

Within the arterial intima there are several proteolytic and lipolytic enzymes and oxidizing agents that are capable of modifying LDL. The activity of these factors is likely responsible for the prominent characteristics of LDL particles isolated from atherosclerotic lesions, namely oxidation, enrichment with sphingomyelin, and self-aggregation. Accumulating evidence points to LDL aggregation and fusion as elements of atherogenic lipid accumulation in the artery wall. Aggregated lipoproteins that appear to be derived from LDL are prominent in early atherosclerotic lesions. Aggregated LDL is taken up by macrophages in vitro at an enhanced rate compared to non-aggregated LDL, leading to macrophage cholesterol accumulation and foam cell formation. Since native LDL particles do not form aggregates, LDL modification appears to be a prerequisite for aggregation and fusion. It is notable that the aggregation/fusion of LDL particles proceeds faster in vitro when they are bound to proteoglycans, and in turn, proteoglycan binding of modified LDL is enhanced as a result of particle aggregation. Studies in vitro have demonstrated that treatment of LDL with sPLA$_2$ and secretory sphingomyelinase (s-SMase), induces LDL aggregation and/or fusion and enhanced retention in the subendothelium (Oorni, K et al., J Lipid Res, 2000. 41(11):1703-14).

The phospholipases A$_2$ (PLA$_2$) family comprises a group of enzymes sharing the common feature of hydrolyzing the fatty acid esterified at the sn-2 position of glycerophospholipids. (Six, D. A. and B. A. Dennis, Biochem. Biophys. Act., 2000. 1488: 1-19). They are generally categorized into cytosolic or secretory forms. The secreted forms of the enzyme are of low molecular weight (14 kDA), highly enriched in disulfide bonds, and require 1-10 mM calcium for activity. The major secreted form present in synovial fluid, termed Group IIA (classically referred to as non-pancreatic secretory PLA$_2$) has been proposed as a mediator of inflammatory responses. During acute or chronic inflammation, the concentration of Group IIA sPLA$_2$ can increase by over 100-fold in inflammatory fluids and plasma. The expression of group IIA sPLA$_2$ is widely distributed in human tissues. In the arterial wall, group IIA sPLA$_2$ is expressed by vascular smooth muscle cells and is associated with heparin sulfate proteoglycans of the ECM Recently, a distinct sPLA$_2$ in macrophages and mast cells has been described. Although it was previously assumed that the sPLA$_2$ in macrophages and mast cells is Group IIA, it is now recognized that Group V sPLA$_2$ is expressed by these cells. Like the Group IIA enzyme, Group V sPLA$_2$ mRNA is greatly induced by proinflammatory stimuli. Group V sPLA$_2$ exhibits high affinity binding to proteoglycans that is mediated by a cluster of cationic residues near the C-terminal end of the enzyme. The studies of Balboa et al. demonstrate that an antisera raised against the synovial sPLA$_2$ (Group IIA) cross-reacts with Group V sPLA$_2$ in P388D$_1$ macrophages. This observation underscores the importance of developing molecular probes and antibodies to distinguish the individual enzymes.

Immunohistochemistry studies have established that sPLA$_2$ is present in normal arterial tissue and increased in atherosclerotic lesions. However, there are some inconsistencies between these reports. In some reports, sPLA$_2$ is predominantly associated with smooth muscle cells, whereas in other reports, a significant amount is detected in macrophages. A possible explanation for the contradictory results may be the variable degree to which available antibodies recognize Group IIA sPLA$_2$ and the related form, Group V sPLA$_2$.

Group V sPLA$_2$ shows a close structural relationship to Group IIA sPLA$_2$. Nevertheless, these enzymes have distinct structural features that may exert important functional differences. Group V sPLA$_2$ contains amino acid variations in the regions that have been shown to be important for the interfacial binding of other sPLA$_2$s. Binding studies using phosphatidylcholine (PC)-coated hydrophobic beads showed that human Group V sPLA$_2$ binds PC membranes more than 50-times more tightly than human Group IIA sPLA$_2$. Indeed, it has been suggested that PC analogues may serve as selective inhibitors for Group V sPLA$_2$, given the low binding affinity of other sPLA$_2$s for PC substrates. In contrast to Group IIA sPLA$_2$, which has been shown to be very ineffective in hydrolyzing PC compared to other phospholipids, kinetic studies show that Group V sPLA$_2$ effectively hydrolyzes PC-containing substrates.

Thus, there is a need for probes and methods to distinguish the Group IIA and Group V sPLA$_2$. There is also a need for methods and compositions to block LDL modifications that lead to LDL aggregation and/or fusion and increased macrophage LDL uptake.

SUMMARY OF THE INVENTION

In one aspect of the invention there is provided an antibody raised against mouse Group V sPLA$_2$ that specifically binds to lesional macrophages.

In another aspect of the invention there is provided a method of assessing the risk of cardiovascular pathology in a patient comprising administering to the patient a monoclonal antibody specific for the human Group V sPLA$_2$ enzyme, said antibody having a detectable label attached thereto; quantifying the amount of Group V sPLA$_2$ in plasma of a human patient and correlating the amount of Group V sPLA$_2$ with the presence of unstable atherosclerotic plaques in the cardiovascular system of the patient.

In yet another aspect of the invention there is provided a method for blocking the formation of aggregates of LDL in a patient, said method comprising administering to a patient an effective amount of an inhibitor of Group V sPLA$_2$.

In another aspect of the invention there is provided a method for preventing atherosclerotic lesion development, said method comprising administering to a patient an effective amount of an inhibitor of Group V sPLA$_2$.

BRIEF DESCRIPTION OF THE DRAWINGS

FIGS. 2A (human) and 2B (mouse) show atherosclerotic lesions stained for either a macrophage-specific antigen (CD68, FA11) or Group V sPLA$_2$. 40× magnification.

DETAILED DESCRIPTION OF THE INVENTION

Several lines of evidence suggest that sPLA$_2$ modification of LDL results in structural alterations of the particle that lead to atherogenic lipid accumulation in the subendothelium. Studies in vitro indicate that lipolysis of LDL with sPLA$_2$ results in partial liproprotein aggregation and increased affinity for proteoglycans. These effects are likely brought about by conformational changes in the apoB-100 moiety of LDL. In addition, sPLA$_2$ modification increases the susceptibility of LDL to hydrolysis by secretory sphingomyelinase (s-SMase). This leads to the accumulation of ceramide within the particles, which can also promote particle aggregation and fusion. Aggregated/fused LDL, which is prominent in atherosclerotic lesions, is one of the most potent inducers of macrophage foam cell formation in vitro. These modified LDL particles are engulfed by macrophages in a process that involves the actin cytoskeleton. Thus, although it has not been directly shown, sPLA$_2$ activity on LDL may promote atherogenesis by generating potent inducers of macrophage foam cells in the arterial subendothelium. Which sPLA$_2$ enzyme(s) produce these effects on LDL in vivo has not been conclusively established.

Group IIA sPLA$_2$ has been shown to be present in atherosclerotic lesions associated with the ECM. Smooth muscle cells appear to be the main source of Group IIA sPLA$_2$ in the arterial wall. Although human recombinant Group IIA sPLA$_2$ is capable of hydrolyzing LDL in vitro, the activity of this enzyme towards LDL is low when compared to the hydrolysis mediated by bee venom sPLA$_2$. It is notable that C57BL/6 mice, a strain susceptible to diet-induced atherosclerosis, lack functional Group IIA sPLA$_2$ as a result of a natural disruption of the gene.

We now show the presence of an additional sPLA$_2$ in atherosclerotic lesions, Group V sPLA$_2$, which is shown herein to be associated specifically with macrophages. These results suggest that the presence of Group V sPLA$_2$ and LDL in the proximity of macrophages leads to the localized production of modified LDL particles that have enhanced capacity for macrophage uptake, which consequently leads to foam cell formation and enhanced atherosclerosis.

The data provided herein suggest that LDL retained in the subendothelium is susceptible to hydrolysis by macrophage-secreted Group V sPLA$_2$ leading to the formation of small, dense LDL particles. These sPLA$_2$-modified LDL particles are susceptible to self-aggregation and fusion. In the arterial wall, sphingomyelinase and/or ECM promotes Group V sPLA$_2$-mediated effects on LDL aggregation and fusion. It is believed that modified LDL particles are taken up by macrophages to a greater extent than native LDL and that the mechanism of uptake of aggregated/fused particles is distinct from receptor-mediated endocytosis of native LDL. Thus, Group V sPLA$_2$ provides an important new target for the treatment of atherosclerotic disease. Use of inhibitors of Group V sPLA2 to prevent the formation of aggregates of LDL is encompassed by the present invention. Such inhibitors include, but are not limited to anti-Group V sPLA$_2$ antibodies, other compounds, such as phosphatidylcholine analogs, that bind to Group V sPLA$_2$ and antisense oligonucleotides that specifically bind to and prevent translation of Group V sPLA$_2$ mRNA. Such compounds can be identified by testing compounds for their ability to bind to Group V sPLA$_2$ and inhibit LDL modification in vitro.

The specific dose of an inhibitor compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Preferably inhibitor compounds or pharmaceutical formulations containing these compounds are in unit dosage form for administration to a mammal. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Figure 1A:
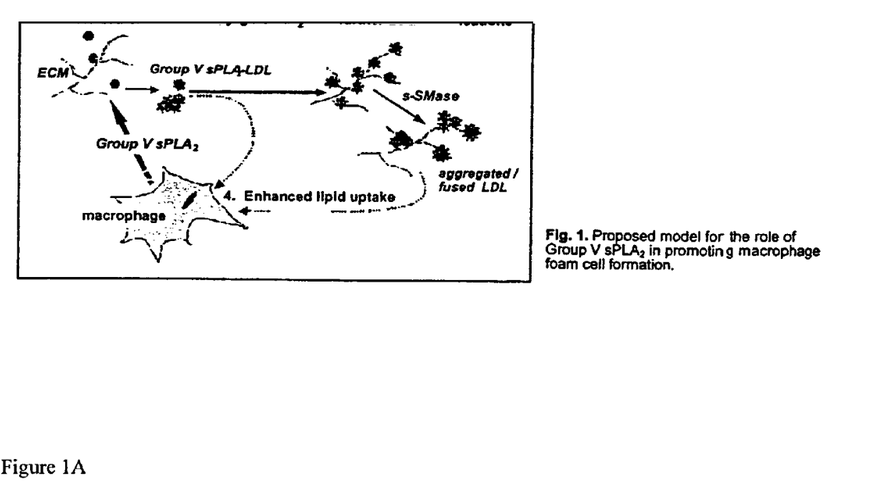
FIG. 1A and FIG. 1B are schematic drawings of a proposed model for the role of Group V sPLA2 in promoting macrophage foam cell formation.
Figure 1B:
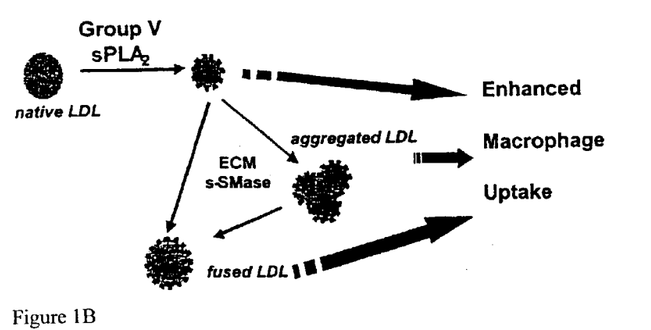

Group V sPLA$_2$ is shown herein to associate specifically with macrophages in human and mouse atherosclerotic lesions. The proposed role of Group V sPLA$_2$ in promoting the accumulation of atherogenic lipid in the developing atherosclerotic plaque is shown in FIG. 1. In the proposed model native LDL in the circulation migrates into the intima and associates with proteoglycans. Group V sPLA$_2$ secreted by macrophages also bind proteoglycans, where it has the capacity to hydrolyze phospholipids on LDL. Group V sPLA$_2$-modified LDL binds proteoglycans with higher affinity and is subject to further modifications, leading to aggregation/fusion of particles. Such LDL modifications promote uptake by macrophages, leading to foam cells.

Figure 2:
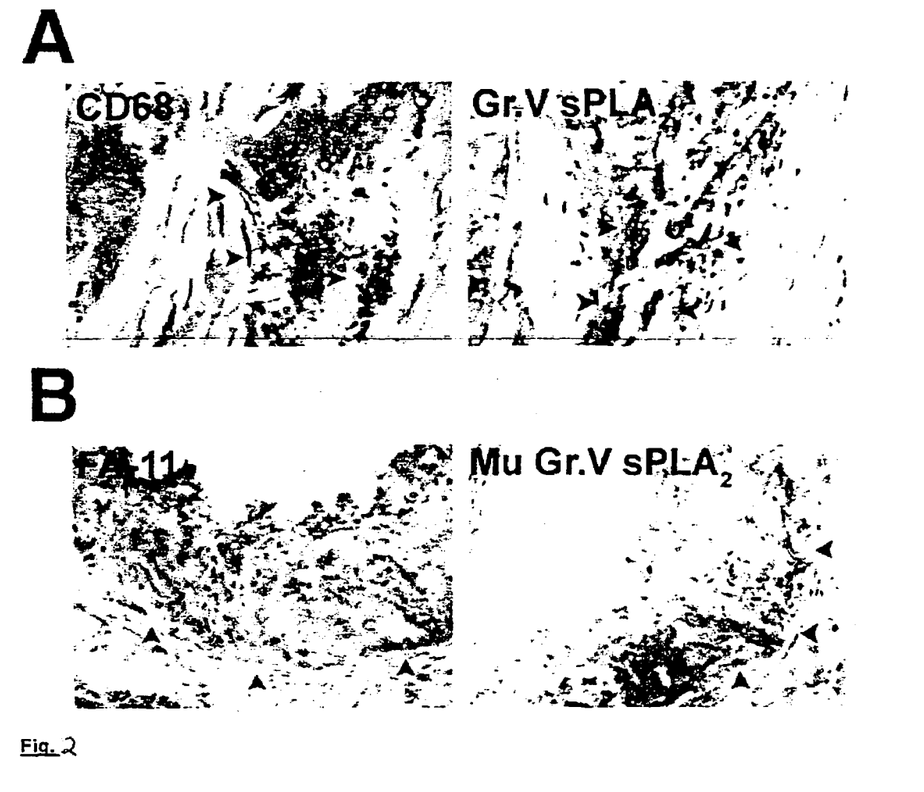

A monoclonal antibody specific for the human Group V enzyme is shown herein to clearly stain macrophages in human atherosclerotic lesions. A polyclonal antibody raised against mouse Group V sPLA$_2$ also demonstrates specific staining of lesional macrophages in a mouse that lacks Group IIA sPLA$_2$. FIG. 2 shows immunostaining of Group V sPLA$_2$ in human (A) and mouse (B) atherosclerotic lesions. FA-11 is a monoclonal antibody which is specific for macrosialin, the mouse homologue of the human macrophage-specific antigen CD68. Serial sections treated with no primary antibody (A) or pre-immune antisera (B) showed no staining. Such antibodies can be used to detect atherosclerotic plaques and to quantitate the amount of Group V sPLA$_2$ in plasma. For example, an anti-Group V sPLA$_2$ antibody may be added to a tissue or plasma sample obtained from a patient in order to detect the presence of Group V sPLA$_2$. The amount of antibody detected can then be correlated to the amount of Group VsPLA$_2$ in the plasma. The anti-Group V sPLA$_2$ specific antibody can be tagged with a detectable label or a second antibody that binds to the anti-Group V sPLA$_2$ antibody can be used to detect the bound anti-group V sPLA$_2$ antibody.

Development of Adenoviral Vector Expressing Mouse Group V sPLA$_2$

Figure 3:
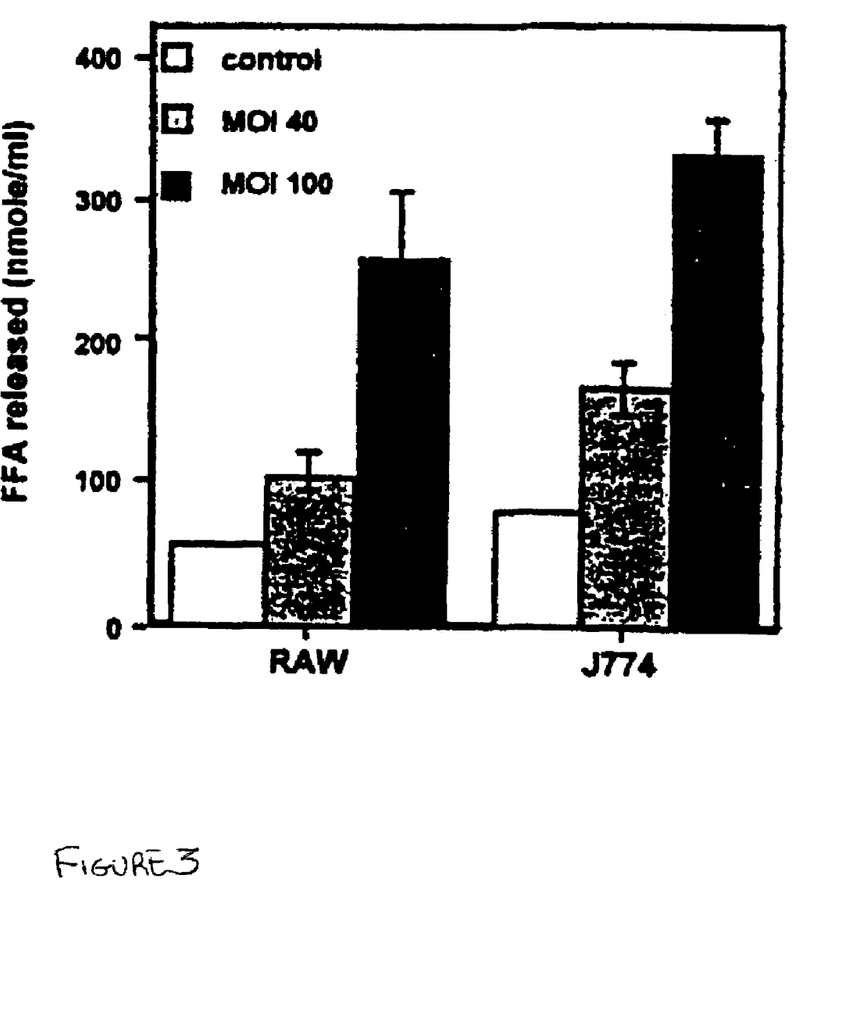
FIG. 3 is a bar graph showing sPLA2 activity produced by control and AdmGV-treated RAW and J774 cells.

Use of viral vectors provides a rapid and efficient technique for over-expressing proteins in macrophages, a cell type that is difficult to stably transfect using plasmid constructs. A replication-deficient adenoviral vector encoding mouse Group V sPLA$_2$, AdmGV, was constructed using methods known to those of skill in the art (see Maniatis, Molecular Cloning, A Laboratory Manual for methods; Genbank for mouse Group V sPLA2 nucleotide sequence) and used to investigate the effect of AdmGV treatment on secreted phospholipase activity in mouse macrophage lines (FIG. 3). Cells were treated with AdmGV at a multiplicity of infection (MOI) of 40 or 100 pfu per cell. After 48 hours of treatment, culture supernatants were collected and assayed for phospholipase activity using a coliormetric assay (WAKO). Mixed micells comprising 1-palmitoyl, 2-oleoyl phosphatidylglycerol (POPG), deoxycholate and noniodet-40 were used as substrate. Values were expressed as the amount of FFA released in the assay per ml of culture media. At the higher dose of adenovirus, sPLA$_2$ activity was increased over baseline values 4.4-fold and 4.2-fold in RAW and J774 cells, respectively.

LDL is Hydrolyzed by Mouse Group V sPLA$_2$ Expressed by Adenoviral Vector

Figure 4:
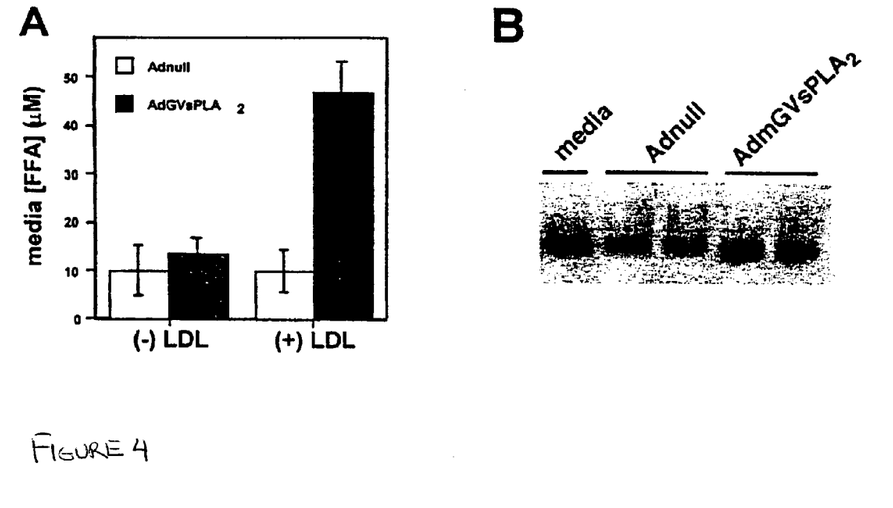
FIG. 4A is a bar graph showing the free fatty acid (FFA) content of media after 24 hours incubation of COS-7 cells (AdmGV-treated and untreated) with 0.2 mg/ml LDL.
FIG. 4B is an autoradiograph showing size distribution of LDL particles after incubation.

Whether Group V sPLA$_2$ expressed by adenoviral vector hydrolyzes LDL was investigated. COS-7 cells were treated with AdmGV or control virus, Adnull. Twenty-four hours after adenovirus treatments, cells were incubated an additional 24 hours with media containing 0.2 mg/ml $^{125}$I-LDL (0.4 µM). The extent of LDL hydrolysis was assessed by measuring the free fatty acid (FFA) content of media. As shown in FIG. 4A, a significant amount of FFA was liberated when LDL was added to Group V sPLA$_2$-expressing cells. The data indicate that approximately 85 molecules of FFA were generated per particle of LDL added. Analysis by non-denaturing gradient gel electrophoresis showed that LDLs incubated with Group V sPLA$_2$-expressing cells migrated as smaller lipoprotein particles compared to control LDLs (FIG. 4B).

Group V sPLA2-Modified LDL Undergoes Spontaneous Aggregation and Promotes Macrophage Foam Cell Formation Partially purified Group V sPLA$_2$ enzyme was prepared from media collected from AdmGV-treated COS cells by sequential chromatograpy on Hi-Trap SP ion-exchange and Hi-Trap heparin columns. Hydrolytic activity of the eluted material was assessed using POPG and LDL as substrates. LDL (0.5 mg/ml; 1 µM) was incubated for 20 hours at 37° C. in buffer containing 6 mM HEPES, 6 mM CaCl$_2$, 2.4 mM MgCl$_2$, 84 mM NaCl and 2% (wt/vol) BSA with and without added enzyme. The amount of FFA acids generated was measured using a colorimetric assay. One unit of GV sPLA$_2$ will generate 1 nmole of FFA per minute using POPG as substrate.

Figure 5:
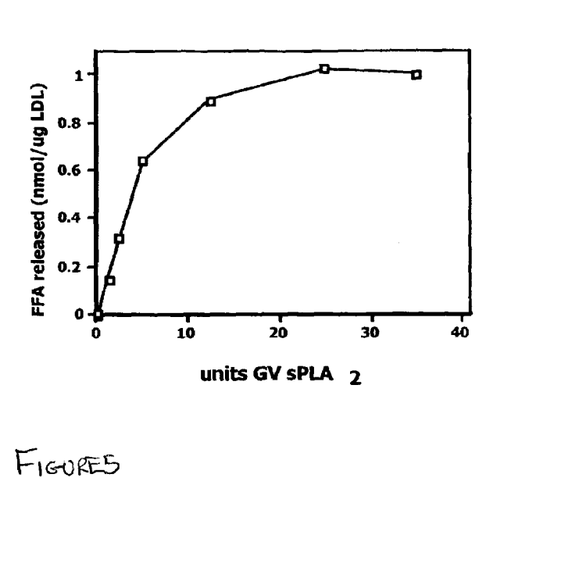
FIG. 5 is a graph showing LDL hydrolysis by purified Group V sPLA$_2$.

At maximal hydrolysis, Group V sPLA$_2$ generated ~1 nmol FFA per µg LDL. Assuming 1.4 nmol phospholipid per µg LDL, this represents ~70% hydrolysis by Group V sPLA$_2$. FIG. 5.

Figure 6:
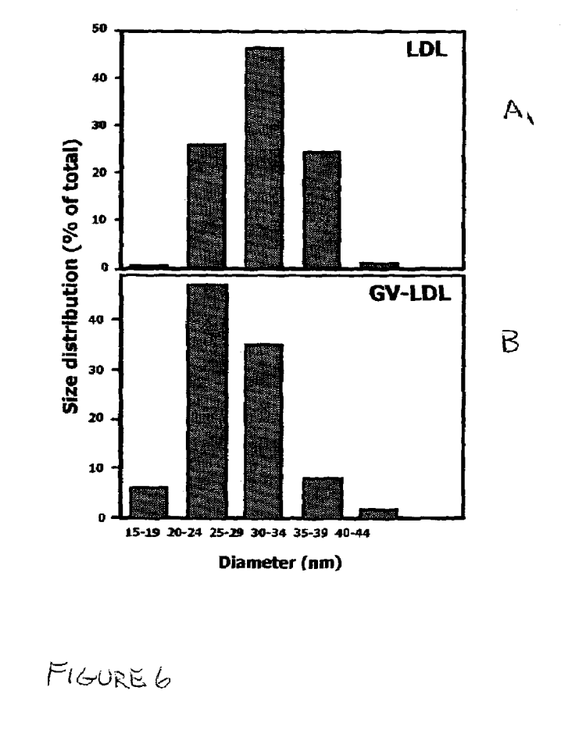
FIGS. 6A and 6B are bar graphs showing the size distribution of unmodified and Group V-modified LDLs as assessed by electron microscopy.

Analysis of LDL particles by electron microsopy after negative staining showed that LDL particles hydrolyzed by Group V sPLA$_2$ are significantly smaller compared to control LDLs. This finding is significant, since small dense LDL particles have increased affinity for proteoglycans and are thereby retained in the vessel wall subendothelium. Mean diameters (±SD) of unmodified and modified LDLs (~200 particles per group) were 27.7 (±0.25) nm and 25.3 (±0.29) nm, respectively (P<0.001). FIGS. 6A and 6B.

Figure 7:
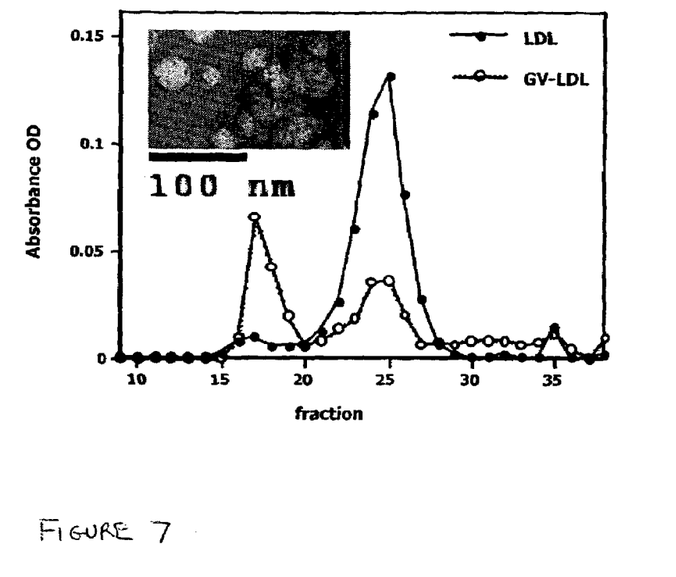
FIG. 7 shows the separation of LDLs before and after treatment with Group V sPLA$_2$ by size exclusion chromatography.

To assess whether hydrolysis leads to spontaneous particle aggregation and/or fusion, LDLs were separated before and after treatment with Group V sPLA$_2$ by size exclusion chromatography. Aggregated/fused particles elute in the void volume of a Superose 6 gel filtration column. The analysis of unmodified LDL and maximally modified LDL showed that a large portion (>50%) of the modified LDL was in an aggregated form. The presence of LDL aggregates was confirmed by electron microscopy. FIG. 7.

Aliquots containing 75 µg unmodified LDL or LDL treated with Group V sPLA$_2$ (~70% phospholipids hydrolyzed) were separated on a Superose 6 column, and the cholesterol content of 0.5 ml fractions was determined. (inset of FIG. 7): Negative staining and electron microscopy of mGV sPLA$_2$-modified LDL particles is shown in FIG. 7.

Figure 8:
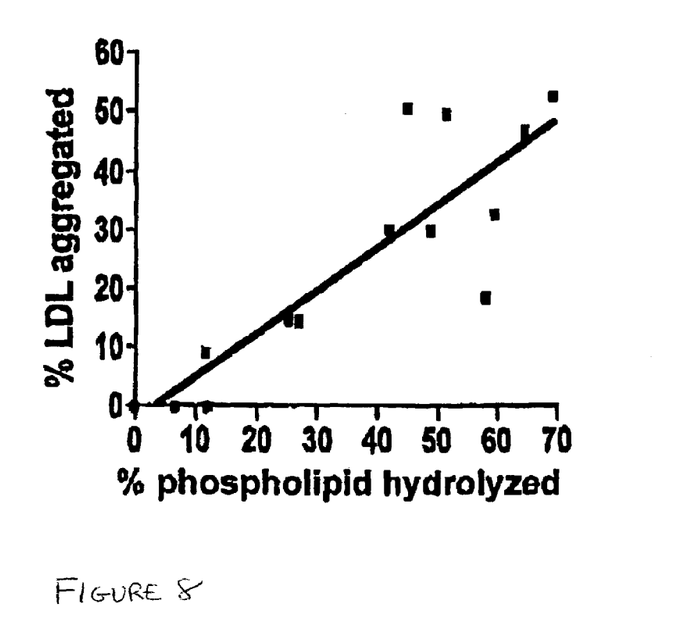
FIG. 8 is a graph showing that the degree of particle aggregation corresponds to the extent of particle hydrolysis.

Further analysis of sPLA$_2$-modified LDL revealed that the degree of particle aggregation is proportional to the percent of phospholipids hydrolyzed. An analysis of Group V sPLA$_2$-hydrolyzed LDL particles shows a positive correlation between the extent of particle hydrolysis and the degree of particle aggregation. FIG. 8.

Figure 9:
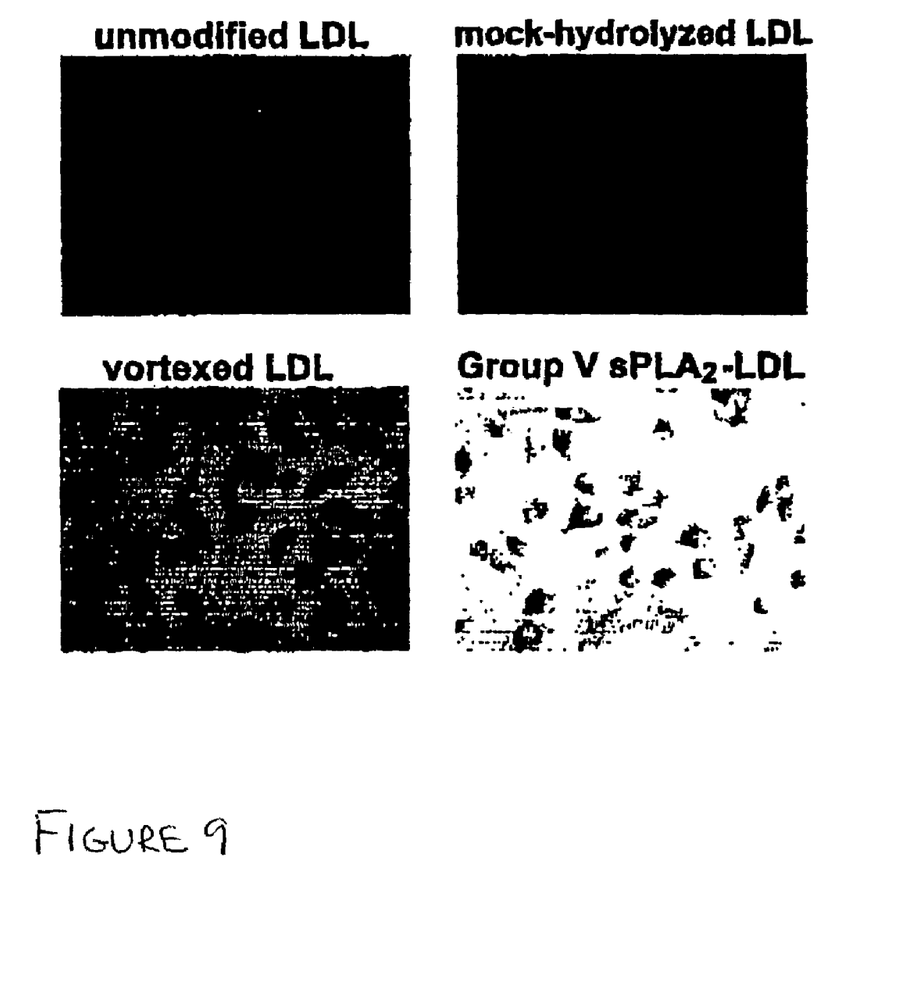
FIG. 9 is a series of photographs of peritoneal macrophages from C57BL/6 mice that were incubated with non-modified (mock) LDL, vortexed LDL, or Group V sPLA$_2$-modified LDL (~30% hydrolyzed) for 48 hours. Cells were stained with Oil Red 0 and analyzed by light microscopy at 40× magnification.

Aggregated LDL, such as that produced by vortexing, has been shown to be the most potent inducer of macrophage foam cells. Kramer, R. M., et al., J Biol Chem, 1989. 264(10): p. 5768-75. Thus, it was of interest to determine whether Group V sPLA$_2$-modified LDL particles that are susceptible to spontaneous aggregation promote foam cell formation in vitro. Peritoneal macrophages from C57BL/6 mice were incubated with non-modified (mock) LDL, aggregated LDL produced by vortexing, or Group V sPLA$_2$-modified LDL (~30% hydrolyzed) for 48 hours. Cells were stained with Oil Red O and analyzed by light microscopy at 40× magnification. FIG. 9. This analysis showed that Group V sPLA$_2$-modified LDL promotes macrophage foam cell formation, providing compelling evidence that this enzyme plays an important role in the initiation and/or progression of atherosclerosis.

Modification of LDL by Group V sPLA$_2$ promotes lipid uptake by peritoneal macrophage cells. Mouse peritoneal macrophage cells were plated (1.8×10$^6$ cells/well) in DMEM complete media on glass cover slips in a 6 well dish. Non-adherent cells were removed by washing with serum free DMEM after 4 hours at 37° C., and adherent cells were stimulated with 1 mM MCSF for 16 hours. Cells were then treated with 200 g/ml unmodified LDL, vortexed LDL, or Group V sPLA$_2$ modified LDL. After 48 hours at 37° C., cells were washed with PBS, fixed with 10% formalin for 10 minutes, and washed with 60% isopropanol. The cells were stained with oil Red O for 30 minutes and washed again with 60% isopropanol. The cells were then visualized with light microscopy at 40× magnification. The results are shown in FIG. 9.

Development of Rabbit Anti-Mouse Group V sPLA$_2$

Figure 10:
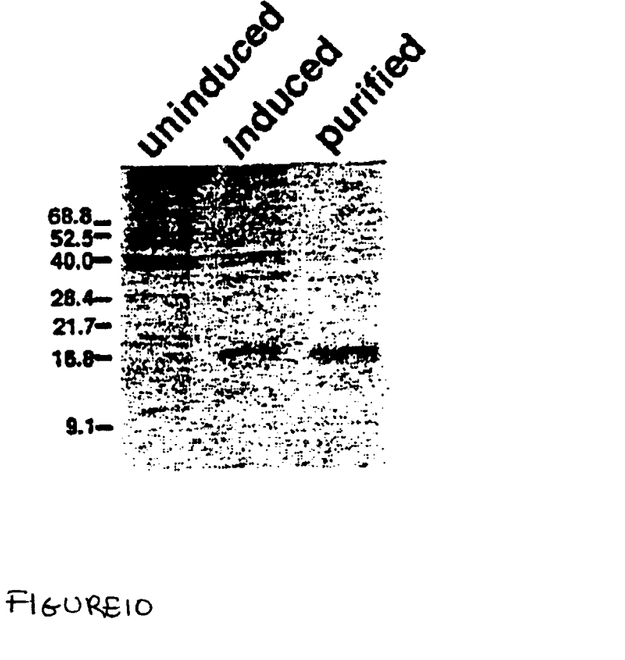
FIG. 10 is a Coomassie blue stained SDS 15% polyacrylamide gel on which mouse Group V sPLA$_2$ expressed in prokaryotic cells was separated. The predicted molecular weight of the Group V sPLA$_2$ fusion protein expressed in the bacterial cells is ~17 kDa.
Figure 11:
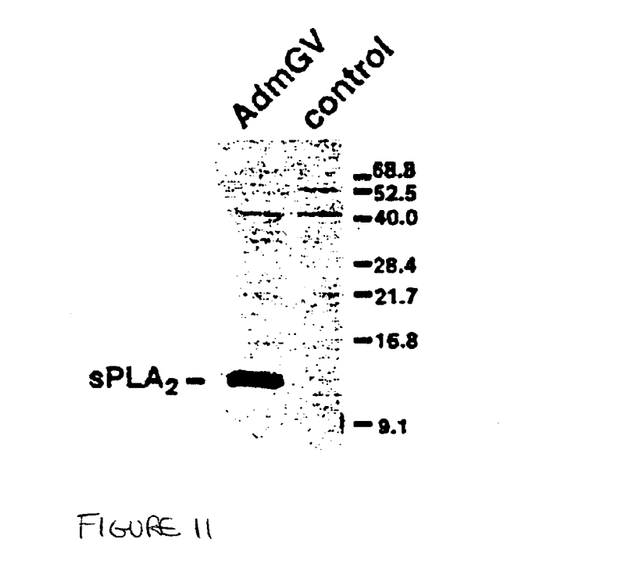
FIG. 11 is an immunoblot of control COS-7 cells and cells after infection with AdmGV, which expresses Group V sPLA$_2$. Cells were infected with an MOI of 40 pfu per cell. Aliquots corresponding to 10 micrograms of protein were separated on 15% SDS PAGE, immunoblotted with rabbit anti-mouse Group V sPLA$_2$, and visulaized by chemiluminescence.

To produce rabbit antisera specific for mouse Group V sPLA$_2$, sequences encoding residues 9-113 were inserted into the bacterial expression plasmid pET22b (Novagen, Madison, Wis.). The expressed protein contained a C-terminal His•Tag, which allowed for one-step purification by affinity chromatography. As shown in FIG. 10, use of this prokaryotic expression system provided an efficient method for producing antigen for immunizing rabbits. The pET system is also used to express full-length mouse Group V sPLA$_2$, which may be purified from bacterial inclusion bodies by gel filtration (Dr. E. A. Dennis, personal communication). The immunoreactivity of rabbit anti-mouse Group V antisera is demonstrated in FIG. 11, which shows immunoblot analysis of total cell lysates from control COS-7 cells and cells infected with adenoviral vector expressing mouse Group V sPLA$_2$. Anti-Group V antisera can be used in the same manner as anti-Group V sPLA2 antibodies to detect and/or quantitate Group V sPLA$_2$ in tissue or serum.

Immunocytochemical Localization of Group V sPLA$_2$ in Human and Mouse Atherosclerotic Lesions As described above, several reports have identified sPLA$_2$ in human atherosclerotic lesions. However, there are inconsistencies in the data as to whether sPLA$_2$ is associated with macrophages or smooth muscle cells (SMC) in lesions. This may be attributed to the cross-reactivity of various antibodies with Group IIA and Group V sPLA$_2$s. Here we used a monoclonal antibody shown to be highly specific for human Group V sPLA$_2$ (Cayman Chemicals, Ann Arbor Mich.) to immunostain human atherosclerotic lesions. This antibody, which does not cross-react with Group IIA sPLA$_2$ displayed strong immunoreactivity (red staining) in lesional macrophages (compare the staining when sections were immunostained with anti-CD68, a macrophage-specific antigen; FIG. 2A, but not in SMC. A newly developed rabbit anti-mouse polyclonal antibody was also generated by art known methods and used to stain lesions in apoE$^{-/-}$ mice. These mice are in the C57BL/6 background, and therefore lack Group IIA sPLA$_2$ due to a frame-shift mutation in exon 3. As shown in FIG. 2B, immunostaining with anti-mouse Group V sPLA$_2$ co-localized with the macrophage-specific monoclonal antibody, FA-11.

What is claimed is:

1. A method of diagnosing the presence of atherosclerotic plaques in a patient comprising:
   (1) obtaining a subendothelial tissue sample from the patient;
   (2) contacting the tissue sample with a first antibody or antibody fragment that specifically binds to human Group V sPLA$_2$; and
   (3) detecting binding of the antibody or antibody fragment to the tissue sample.

2. The method of claim 1 wherein the first antibody or antibody fragment has a detectable label attached thereto.

3. The method of claim 1 wherein the first antibody or antibody fragment is detected by contacting the tissue sample with a second antibody that binds to the first antibody or antibody fragment, wherein said second antibody has a detectable label attached thereto.

4. The method of claim 1 wherein the first antibody or antibody fragment is detected by contacting the sample with a chemical entity that binds to the first antibody or antibody fragment, wherein the chemical entity has a detectable label attached thereto.

* * * * *